(12) United States Patent
Haverkost et al.

(10) Patent No.: US 10,029,070 B2
(45) Date of Patent: Jul. 24, 2018

(54) CRESCENT CHANNEL DYE FLOW ENABLED GUIDE CATHETERS

(71) Applicant: BOSTON SCIENTIFIC SCIMED, INC., Maple Grove, MN (US)

(72) Inventors: Patrick A. Haverkost, Brooklyn Center, MN (US); Martin R. Willard, Burnsville, MN (US); Peter G. Edelman, Maple Grove, MN (US); Jonathan S. Stinson, Plymouth, MN (US); Jacob D. Edick, Minneapolis, MN (US); Joel N. Groff, Delano, MN (US); Anthony F. Tassoni, Jr., Ramsey, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 610 days.

(21) Appl. No.: 14/609,141

(22) Filed: Jan. 29, 2015

(65) Prior Publication Data
US 2015/0217085 A1 Aug. 6, 2015

Related U.S. Application Data

(60) Provisional application No. 61/935,159, filed on Feb. 3, 2014.

(51) Int. Cl.
*A61M 25/00* (2006.01)
*A61M 31/00* (2006.01)

(52) U.S. Cl.
CPC .... *A61M 25/0032* (2013.01); *A61M 25/0012* (2013.01); *A61M 25/0015* (2013.01); *A61M 25/0045* (2013.01); *A61M 31/005* (2013.01); *A61M 25/005* (2013.01); *A61M 25/007* (2013.01); *A61M 2210/12* (2013.01)

(58) Field of Classification Search
CPC ............ A61M 25/0045; A61M 25/005; A61M 25/0012; A61M 25/0032; A61M 25/007; A61M 25/0015; A61M 2210/12
See application file for complete search history.

(56) References Cited

U.S. PATENT DOCUMENTS 4,578,061 A * 3/1986 Lemelson ............ A61N 5/1014
604/170.01
5,063,018 A * 11/1991 Fontirroche ...... A61M 25/0009
156/244.13

(Continued)

FOREIGN PATENT DOCUMENTS

EP 0912212 A1 5/1999
EP 1144039 A2 10/2001

(Continued)

*Primary Examiner* — Bhisma Mehta
*Assistant Examiner* — Jenna Zhang
(74) *Attorney, Agent, or Firm* — Seager, Tufte & Wickhem, LLP

(57) ABSTRACT

An intravascular catheter is disclosed that includes an elongated shaft defined by a wall including at least one port extending through the wall into a lumen. At least one channel may be defined between layers of polymer making up the catheter shaft. The channel extends along at least a portion of the shaft and is in fluid communication with the port. Outer and inner diameters of the catheter may be substantially constant along the length of the catheter.

11 Claims, 23 Drawing Sheets

(56) References Cited

U.S. PATENT DOCUMENTS

| | | | |
|---|---|---|---|
| 5,171,305 A * | 12/1992 | Schickling | A61M 25/0119 604/271 |
| 5,238,004 A | 8/1993 | Sahatjian et al. | |
| 5,244,619 A * | 9/1993 | Burnham | A61M 25/0012 264/171.2 |
| 5,782,811 A * | 7/1998 | Samson | A61M 25/005 604/524 |
| 5,879,499 A * | 3/1999 | Corvi | A61M 25/0012 156/173 |
| 6,379,365 B1 | 4/2002 | Diaz | |
| 6,508,803 B1 | 1/2003 | Horikawa et al. | |
| 2002/0156460 A1 | 10/2002 | Ye et al. | |
| 2005/0004441 A1 | 1/2005 | Chen et al. | |
| 2005/0113798 A1 | 5/2005 | Slater et al. | |
| 2007/0088323 A1 | 4/2007 | Campbell et al. | |
| 2012/0123258 A1 | 5/2012 | Willard | |
| 2012/0296367 A1 | 11/2012 | Grovender et al. | |

FOREIGN PATENT DOCUMENTS

| | | | | |
|---|---|---|---|---|
| WO | WO 9843696 A1 * | 10/1998 | | A61B 17/12022 |
| WO | WO 9965557 A2 * | 12/1999 | | A61M 25/0009 |

* cited by examiner

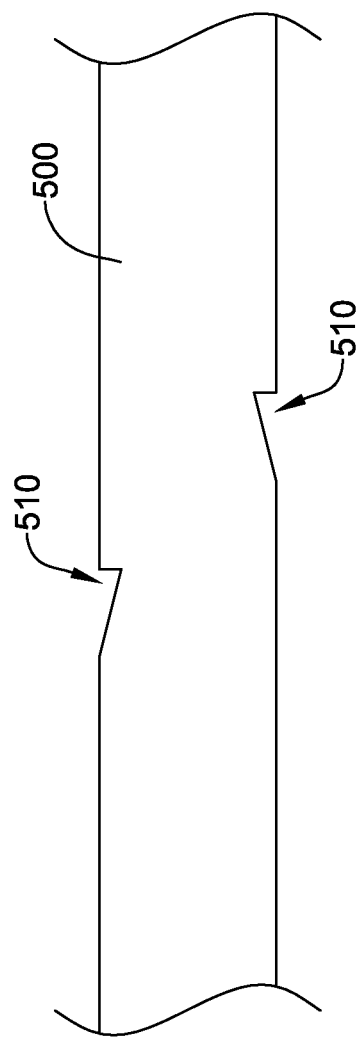

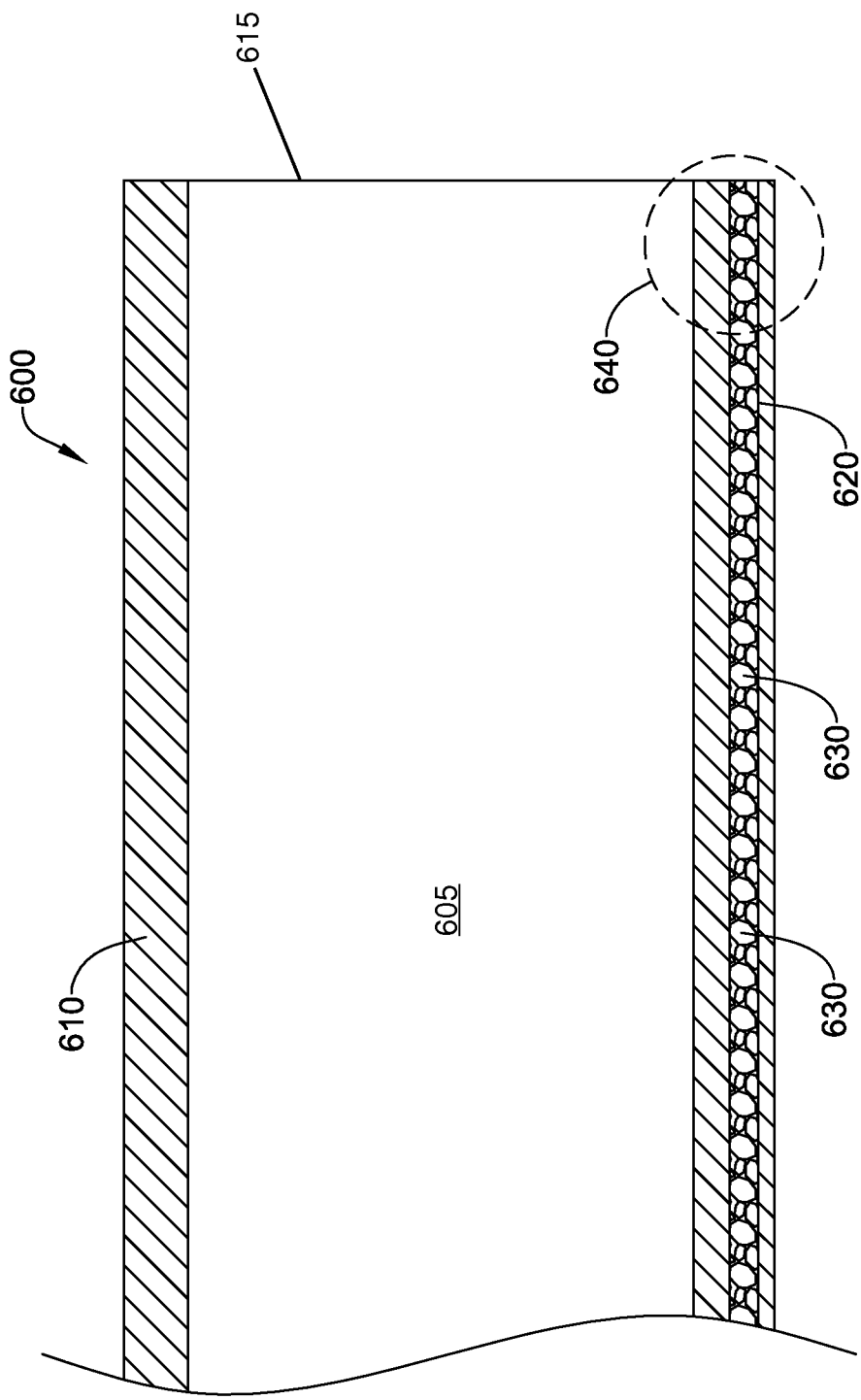

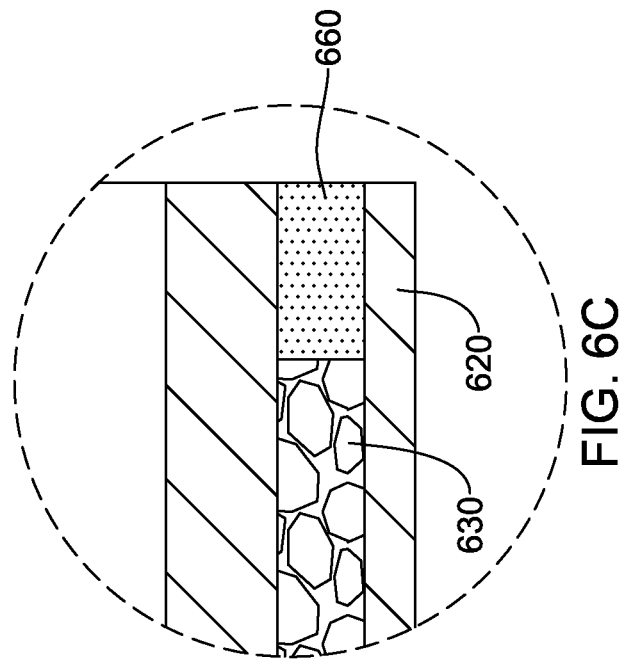
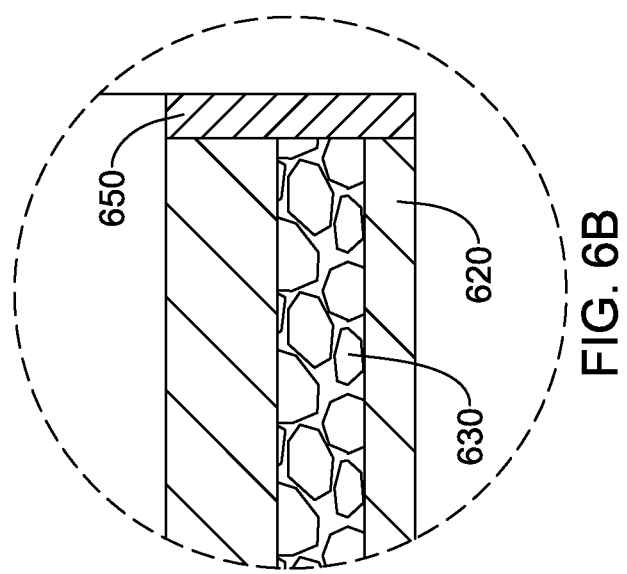

CRESCENT CHANNEL DYE FLOW ENABLED GUIDE CATHETERS

CROSS-REFERENCE TO RELATED APPLICATIONS

This application claims priority under 35 U.S.C. § 119 to U.S. Provisional Application Ser. No. 61/935,159, filed Feb. 3, 2014, the entirety of which is incorporated herein by reference.

TECHNICAL FIELD

The present disclosure is directed to medical devices and methods for making and using the medical devices. More particularly, the present disclosure relates to medical devices for providing contrast medium or fluid.

BACKGROUND

A wide variety of intracorporeal medical devices have been developed for medical use, such as for intravascular use. Some of these devices include guidewires, catheters, and/or other apparatus. These devices can be manufactured by any one of a variety of different manufacturing methods, and may be used according to any one of a variety of methods. Of the known medical devices and methods, each has certain advantages and disadvantages. There is an ongoing need to provide alternative medical devices as well as alternative methods of manufacturing and using medical devices.

SUMMARY

An intravascular catheter may have an elongated shaft defined by a wall and having a proximal end, a distal end, and a lumen extending therebetween. The shaft may include a length extending between the proximal and distal ends and at least one port extending through the wall into the lumen. A first layer may be disposed over the shaft extending from the proximal end of the shaft over the port to a distal terminus. The catheter may include a second layer disposed over the first layer, a third layer disposed over the second layer, and at least one channel defined between the second and third layers. The channel may extend along at least a portion of the shaft and into the port. The channel may extend around less than the entire circumference of the shaft. An outer diameter of the third layer may be substantially constant along the length of the shaft.

Another intravascular catheter may include an elongate shaft having a proximal end, a distal end and a lumen extending therebetween. The elongate shaft may include an inner liner having a wall and defining the lumen. The inner liner may include at least one port extending through the wall into the lumen. The elongate shaft may include a braid disposed over the liner and extending over the port. The elongate shaft may further include a first polymer layer disposed over the braid and a second polymer layer disposed over the first polymer layer. The elongate shaft may further include at least one channel defined between the first and second polymer layers and extending along the elongate shaft and into the port. An inner diameter and an outer diameter of the elongate shaft may be substantially constant along an entire length of the shaft.

A method of manufacturing a catheter may include placing a first layer over a mandrel having a proximal region and a distal region, creating at least one port through the first layer. The method may further include placing a braid over the first layer and over the port, placing a first polymer layer over the braid, and placing a crescent shaped mandrel over the first polymer layer. The distal end of the crescent shaped mandrel may extend through the first polymer layer, the braid, and the port. The method may also include placing a second polymer layer over the crescent shaped mandrel and over the first polymer layer, and reflowing the first and second polymer layers, thereby creating a catheter with substantially constant inner and outer diameters. The method further includes removing the mandrels.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 5A is a longitudinal cross-sectional side view of an example mandrel;

FIG. 6A is a longitudinal cross-sectional side view of another example guide catheter;

FIGS. 6B and 6C are partial longitudinal cross-sections taken from alternative embodiments of the distal end of FIG. 6A;

Figure 1:
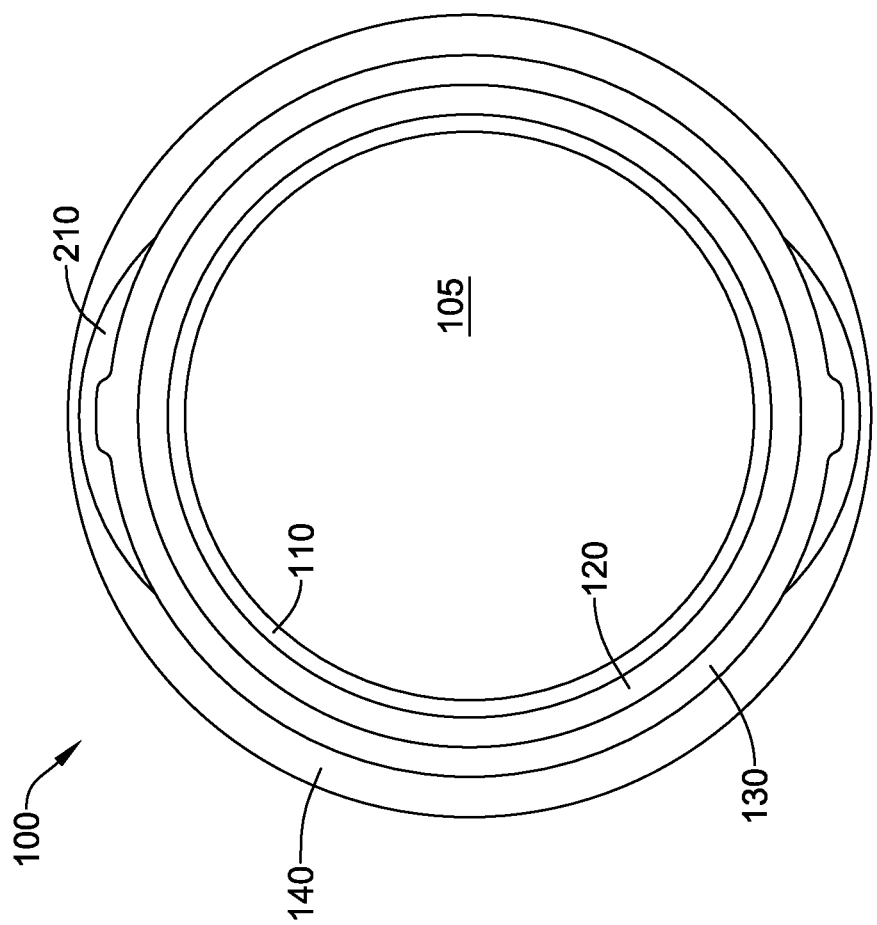
FIG. 1 is a transverse cross-sectional view of a portion of an example guide catheter.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

The following detailed description should be read with reference to the drawings, in which similar elements in different drawings are identified with the same reference numbers. The drawings, which are not necessarily to scale, depict illustrative embodiments and are not intended to limit the scope of the disclosure.

Most catheter based tools and devices have at least one element that may dictate its maximum profile and guide catheter capability. In addition, users often require visibility and will use contrast injection from the guide catheter while the device or tool is within the lumen of the guide catheter to see a location within a vessel of the patient. The largest profile element of the device in use may restrict a sufficient flow of contrast medium from a proximal end of the device by occupying almost all of the inner space of the catheter and leaving no space for the contrast medium to flow. The user may either withdraw the device from the lumen of the guide catheter to inject the contrast medium, or use a larger guide catheter for the procedure so as to allow for sufficient contrast flow. However, larger profile guide catheters may not be suitable for use in all medical procedures.

Thus, it may be beneficial to provide alternative medical devices as well as alternative methods for manufacturing and using medical devices that address at least some of the above issues. Some of the disclosed embodiments are therefore directed to several alternative designs of medical device structures and assemblies, as well as methods of making and using the alternative medical device structures and assemblies.

Some embodiments disclosed herein are directed to a catheter based device for use in a guide catheter. Visibility and contrast injection from the guide catheter while the device or tool is within the lumen of the guide catheter is provided by dedicating small dye flow channels in the design without impacting the inner diameter, outer diameter or other performance attributes of the medical device.

The present disclosure addresses at least some of the above issues by disclosing systems, medical devices and methods of manufacturing the medical devices that may be used in a guide catheter while still allowing for flow of contrast media to a target location. Some of these embodiments dedicate small channels in the design without impacting the inner diameter, outer diameter, or other performance attributes of the guide catheter.

The present disclosure also provides methods of manufacturing the guide catheter that include a crescent shaped channel to enable contrast medium or solution flow within the guide catheter without altering the inner or outer diameter. During the construction of such a guide catheter, channels can be created within the layers of the polymers to ensure the free flow of contrast media from the proximal end of the catheter to a target location at a distal end of the catheter. Various exemplary embodiments are described below with reference to various figures.

FIG. 1 is a transverse cross-sectional view of a portion of an exemplary guide catheter 100, in accordance with an embodiment of the present disclosure. The guide catheter 100 includes an elongate shaft (e.g., 610 in FIG. 6A) having an inner diameter defined by a wall or an inner liner 110. Hereinafter, the wall and the inner liner 110 may be used interchangeably without changing its meaning and functionality. The elongate shaft includes a proximal end, a distal end, and a lumen 105 extending therebetween. The elongate shaft has a length that extends between the proximal end and the distal end of the elongate shaft. In at least one embodiment, an inner diameter of the elongate shaft may be substantially constant along its length. The shaft may also include at least one port (e.g., port 112 in FIG. 3A) extending through the inner liner 110 into the lumen 105. In some embodiments, the inner liner 110 may be formed using a suitable material capable of receiving any therapeutic devices that may be inserted through the lumen 105. Examples of such materials may include, but are not limited to, polytetrafluoroethylene (PTFE), polyethylene terephthalate (PET), or the like. Other materials such as polyimides are also commonly used as an inner liner 110.

As shown, the guide catheter 100 may also include a first layer disposed over the inner liner 110. In at least one embodiment, the first layer may include a braid 120 defining a number of interstices. The braid 120 may be disposed over the elongate shaft and may extend from the proximal end of the shaft over the port 112 to a distal terminus. The braid 120 may be formed using suitable biocompatible materials including, but not limiting to, stainless steel, aluminum, gold, platinum, titanium, PET, polyvinyl chloride (PVC), polycarbonate, nylon, silk, polyether ether ketone (PEEK), liquid crystalline polymer (LCP), or the like.

A first polymer layer 130 may be disposed over the braid 120. A second polymer layer 140 may be disposed over the first polymer layer 130. The first polymer layer 130 and the second polymer layer 140 may be formed using suitable biocompatible materials that may provide sufficient smoothness to these layers. Examples of such materials may include, but are not limited to, polymers such as, polyethylene, polyurethane, silicone, polyether blocked amide, nylons, polyesters, or the like.

The guide catheter 100 may also include at least one channel 210 defined between the first polymer layer 130 and the second polymer layer 140. In some embodiments, the at least one channel 210 includes two or more channels spaced apart around a circumference of the elongate shaft. The channel 210 may be crescent shaped. As shown in FIG. 1, a cross section of the channel 210 taken perpendicular to a longitudinal axis of the elongate shaft has a substantially crescent shaped cross section. In some embodiments, the channel 210 may extend along at least a portion of the elongate shaft, through an interstice of the braid 120, through the port 112 in the inner liner 110 and into the lumen 105. The at least one channel 210 may extend around less than an entire circumference of the shaft. FIG. 1 illustrates an embodiment of a guide catheter 100 having two channels 210 spaced apart on opposing sides of the shaft.

Figure 2A:
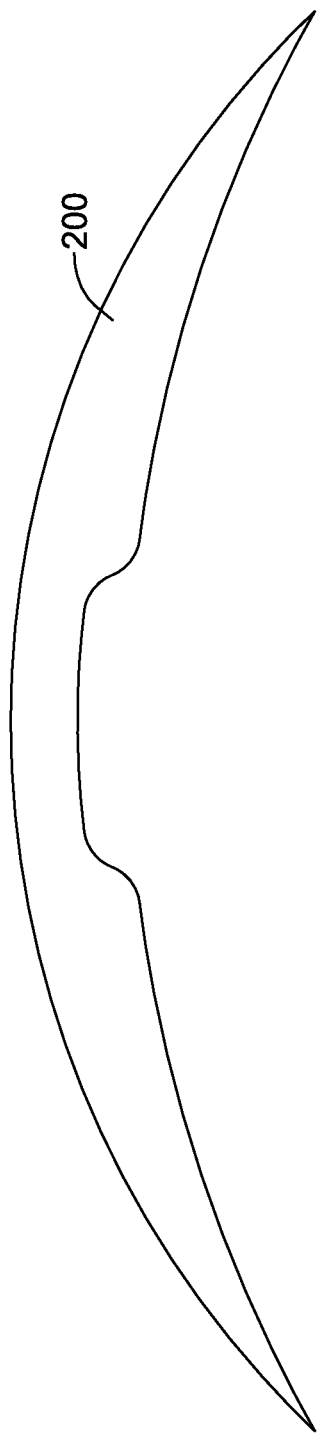
FIG. 2A is a transverse cross-sectional view of a crescent shaped mandrel.

FIG. 2A is an enlarged transverse cross sectional view of a crescent shaped mandrel 200. The crescent shaped mandrel 200 may be used to create a crescent shaped lumen or channel 210 in the guide catheter 100 of FIG. 1. The crescent shaped mandrel 200 may have a highly smooth surface. The crescent shaped mandrel 200 may be coated with a non-stick coating to aid in extracting the mandrel from the formed guide catheter 100. In some embodiments, the non-stick coating may be a PTFE coating, for example, a hard coat such as DR-55 (RothGreaves, Long Lake, Minn.). In other embodiments, a mold release agent may be used to coat the crescent shaped mandrel 200 to aid in its removal. The crescent shaped mandrel 200 may be used to create one or more very fluid channels 210 that extend along the guide catheter between the first polymer layer 130 and the second polymer layer 140. At a distal end thereof, the channel 210 may cross the first polymer layer 130, braid 120, and inner liner 110 and enter the lumen 105 through a port 112. The crescent shaped channel 210 may increase the likelihood that contrast medium, such as dye, can be delivered to the tip of the guide catheter 100, even if the inner liner 110 of the guide catheter 100 is fully occluded by an interventional device or device feature.

Figure 2B:
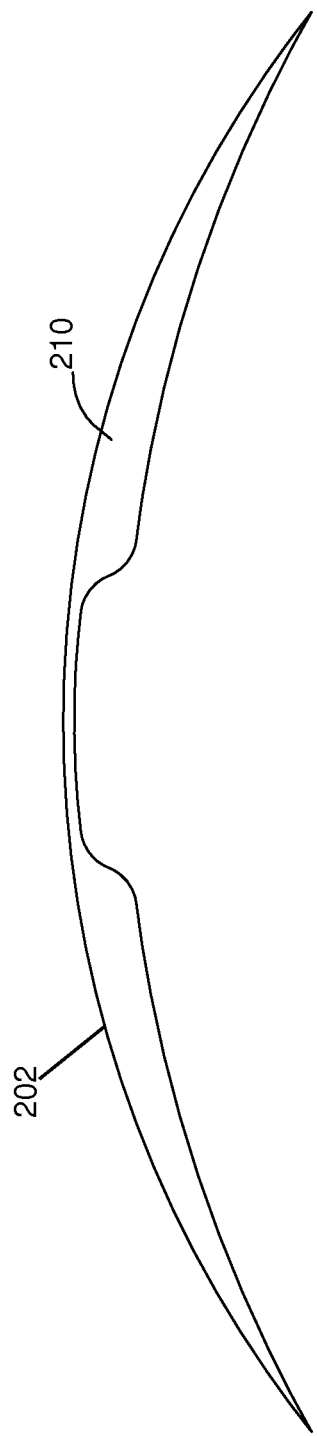
FIG. 2B is a transverse cross-sectional view of a channel, formed with the mandrel of FIG. 2A, in a compressed configuration.

FIG. 2B illustrates a flattened shape the channel 210 may achieve when the catheter 100 is in a bent configuration. While the channel 210 may be compressed when the catheter 100 is bent, complete collapse of the channel 210 is prevented even when an upper surface 202 is deflected downwards. While the upper surface 202 may contact the lower surface in the middle of the channel 210, due to the shape of the channel, the side portions remain open as shown in FIG. 2B. In this manner, the channel 210 remains open for transporting contrast media even when the catheter 100 is bent and the channel 210 is compressed.

Figure 3A:
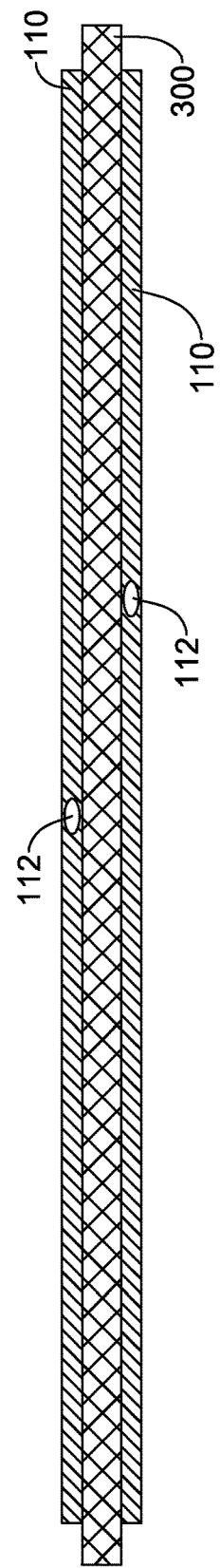
FIGS. 3A-3G are longitudinal cross-sectional side views showing steps of manufacturing an example guide catheter.

FIGS. 3A-3G illustrate longitudinal cross section views showing steps of manufacturing an exemplary guide catheter. As shown in FIG. 3A, the inner liner 110 is placed over a mandrel 300. The inner liner 110 may be formed using suitable biocompatible materials, metals or alloys. Examples of suitable biocompatible materials, metals or alloys may include, but are not limited to, stainless steel, aluminum, gold, platinum, titanium, PTFE (e.g., Teflon®, available from DuPont Co.), PET, PVC, polycarbonate, nylon, silk, PEEK, and so forth.

At least one port 112 may be cut into the inner liner 110 of the guide catheter 100. The port 112 may be cut using a laser. The at least one port 112 is a hole having a small diameter extending completely through the inner liner 110. Multiple ports 112 may be formed in the inner liner 110, and the ports 112 may be staggered along the catheter, as shown in FIG. 3A. In other embodiments, ports 112 may be created along the length of the inner liner 110. In some embodiments, the at least one port 112 includes a plurality of ports 112 offset longitudinally and spaced apart around the circumference of the inner liner 110. The ports 112 may be located in any desired region of the catheter 100. In some embodiments, the ports 112 may be in the distal region of the catheter 100. In other embodiments, one or more port 112 may be in the proximal region of the catheter 100. In still other embodiments, a plurality of ports 112 may be spaced apart along the length of the catheter 100. The at least one port 112 may have a suitable shape or size including but not limited to, circular, rectangular, polygonal, irregular, and so forth. For example, the at least one port 112 may have an "S" shape extending longitudinally along the inner liner 110. In some embodiments, differently shaped ports 112 may be present in the inner liner 110. In one embodiment, at least two ports 112 are created in the inner liner 110, such that the ports 112 are disposed on opposite sides relative to each other, and are longitudinally spaced apart, as shown in FIG. 3A.

Figure 3B:
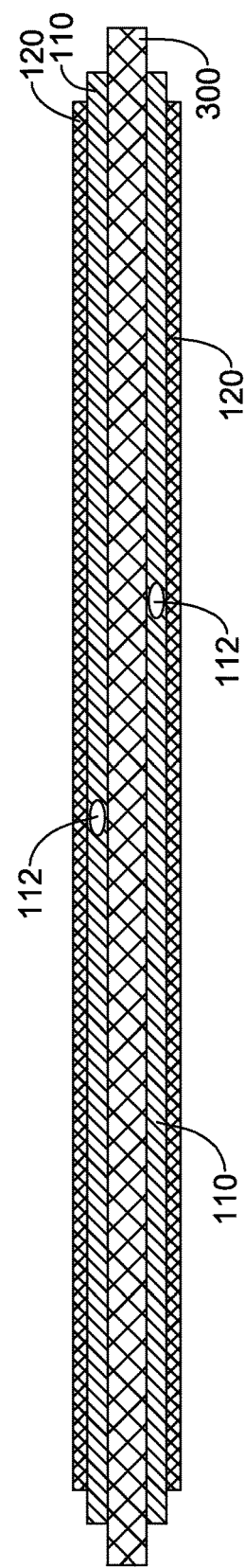

As shown in FIG. 3B, a braid 120 may be placed over the inner liner 110 and over the port 112. The braid 120 may be a mesh like structure that is placed over the inner liner 110. The braid 120 may have a high braid angle and may define diamond shaped interstices. The diamond shaped interstices may be relatively short in a longitudinal direction and may be relatively wide in a radial direction. The braid interstices allow for the flow of melted and/or heated polymers through the braid 120 such that the braid 120 is embedded within the polymer of the catheter shaft. The diamond shaped braid interstices may allow the crescent shaped mandrel 200 to pass through the braid 120 without disrupting the braid structure.

Figure 3C:
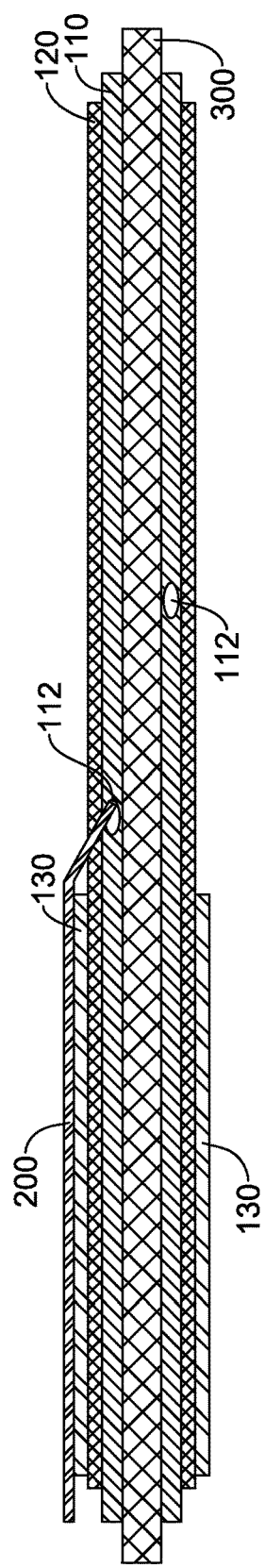
Figure 3D:
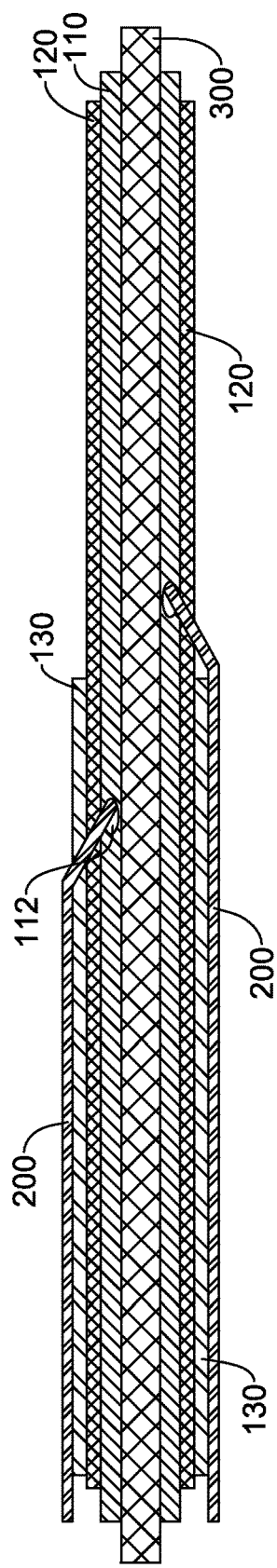
Figure 3E:
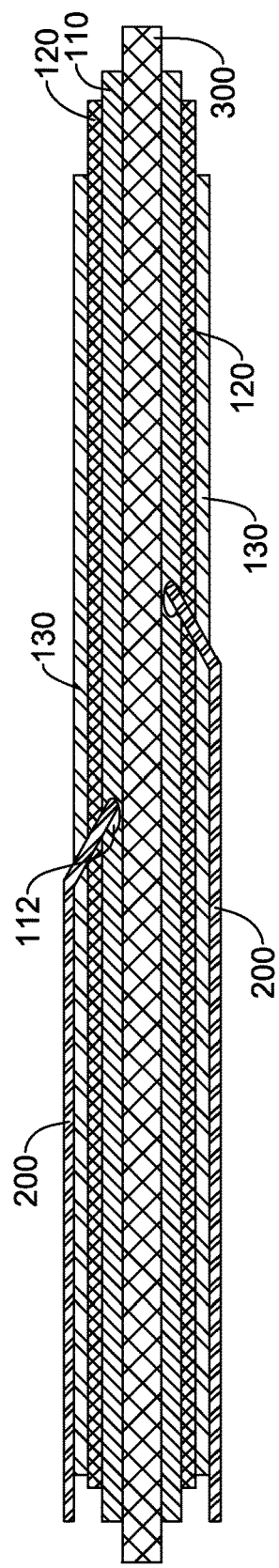

Thereafter, as shown in FIG. 3C, a second layer including the first polymer layer 130 may be placed over the braid 120. In some embodiments, multiple extrusions of polymeric material of varying durometer (e.g. 72D-62D-55D) may be provided or placed over the braid 120, resulting in a guide catheter having a varying stiffness along its length. Then, one or more crescent shaped mandrel 200 may be placed over the first polymer layer 130, as shown in FIG. 3C. The distal end of the crescent shaped mandrel 200 may be inserted through the braid 120 interstice and through the port 112 in the inner liner 110. In some embodiments, a locking mechanism may be provided in the mandrel 300 so that a distal tip of the crescent shaped mandrel 200 may be locked to the mandrel 300. Additional polymer tubular sections of the first polymer layer 130 may be placed over the braid 120 and additional crescent shaped mandrels 200 may be placed over the first polymer layer 130 adjacent the remaining ports 112, as shown in FIG. 3D. In some embodiments, two crescent shaped mandrels 200 may be placed over the first polymer layer 130 such that a distal end of each crescent shaped mandrel 200 extends through the at least one port 112, as shown in FIG. 3E. After all crescent shaped mandrels 200 are placed, additional sections of first polymer layer 130 are added, extending along the length of the catheter shaft, as shown in FIG. 3E. In one embodiment, the first polymer layer 130 may be reflowed over the braid 120. The polymeric material forming the first polymer layer 130 may melt and flow in the interstices of the braid 120. The polymeric material may be heated or reflowed over the braid 120 using suitable tool including, but not limiting to, a tube oven, an FEP Teflon® heat shrink tool, customized reflow air tool, and so forth. In some embodiments each segment of first polymer layer 130 is heated or reflowed over the braid after addition to the catheter.

Figure 3F:
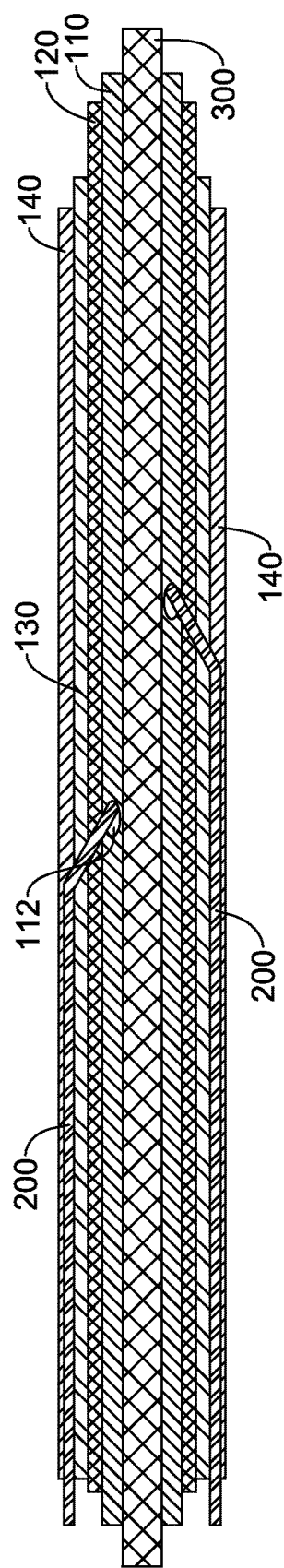

As shown in FIG. 3F, the second polymer layer 140 is placed over the crescent shaped mandrel 200 and over the first polymer layer 130. The first and second polymer layers 130, 140 are reflowed over the crescent shaped mandrel 200, thereby creating a catheter with substantially constant inner and outer diameters, as shown in FIG. 3F. In at least some embodiments, portions of the guide catheter 100 may also be doped with, made of, or otherwise include a radiopaque material.

Figure 3G:
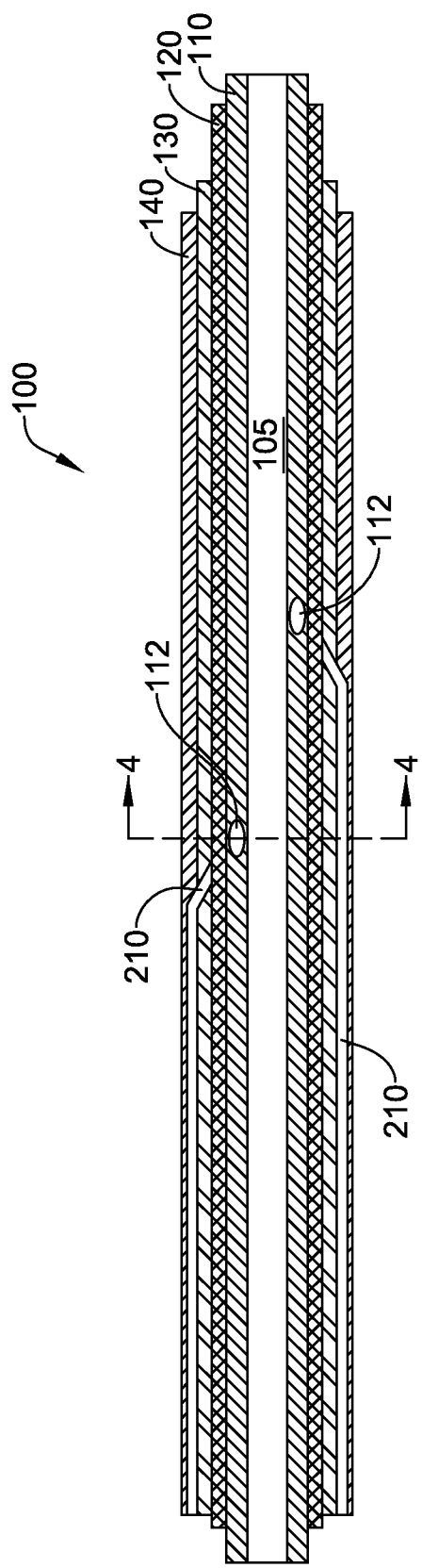
Figure 4:
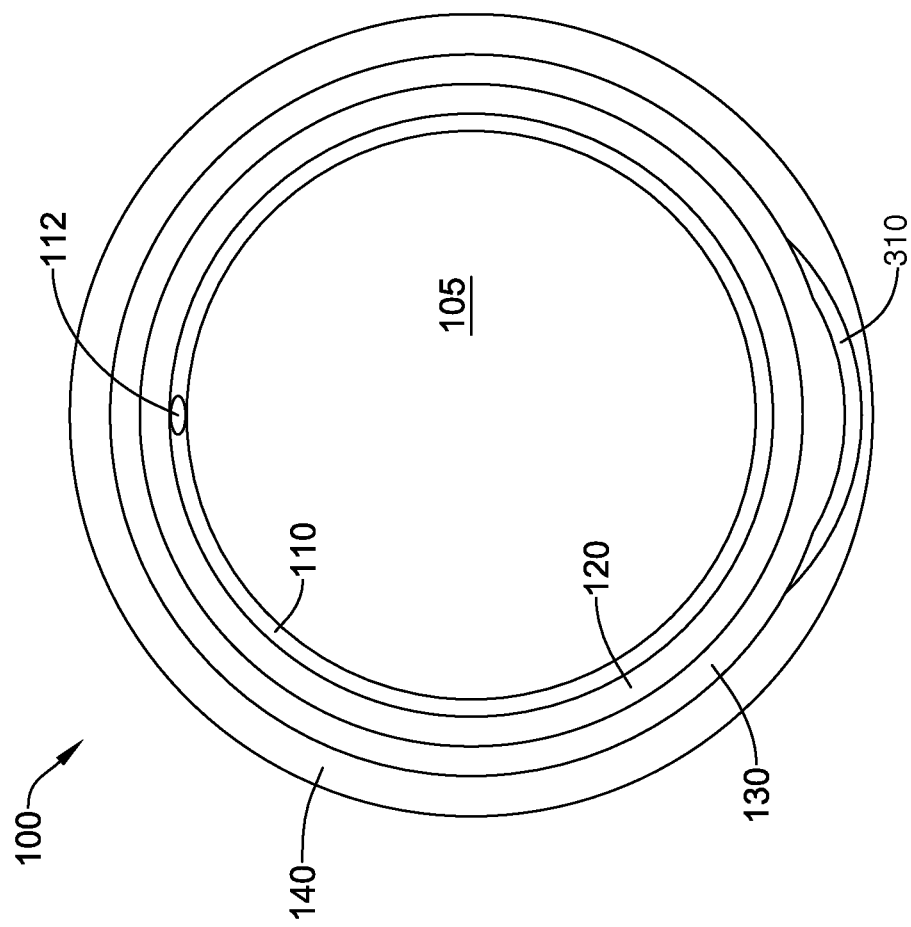
FIG. 4 is a cross-sectional view taken through line 4-4 in FIG. 3G.

After the polymer layers 130, 140 have been reflowed, both the mandrels, i.e., the crescent shaped mandrels 200 and the mandrel 300, are removed as shown in FIG. 3G, forming a guide catheter 100 with an inner lumen 105 and one or more channels 210. The channels 210 extend along the length of the catheter between first and second polymer layers 130, 140, and are in flow communication with the inner lumen 105 at the ports 112. In some embodiments, the channels 210 extend from the proximal end of the catheter 100 to the ports 112. In other embodiments, the channels 210 have proximal ports (not shown) extending through the second polymer layer 140 to the exterior of the catheter at a position proximal of the ports 112. FIG. 4 is a cross-sectional view taken through line 4-4 in FIG. 3G, showing a channel 310 and a port 112. The channel 310 illustrated in FIG. 4 is an alternatively shaped channel, with a more gradual curved inner surface as compared to channel 210 illustrated in FIGS. 1-2B.

In some embodiments the thickness of the first polymer layer 130 and the second polymer layer 140 combined is minimized to achieve a catheter with desired inner and outer diameters. Half of the total polymer thickness may be used for the first polymer layer 130 and half may be used for the second polymer layer 140. In other embodiments, a larger percentage of the total desired polymer thickness may be used for the first polymer layer 130, leaving a thinner polymer layer over the channels 210.

Catheters of between 6 and 10 French may be created, with inner diameters ranging from 0.07 to 0.69 inches (0.1778 to 1.753 centimeter). When multiple channels 210 are created in the catheter 100, the channels 210 may be the same size or channels 210 of differing size may be created, using crescent shaped mandrels 200 of differing sizes. In one embodiment, a single channel 210 is created. In other embodiments, two channels 210 are created on opposite sides of the catheter. Other embodiments include two channels 210 created less than 180 degrees apart. The channels 210 may have ports 112 located at the same longitudinal position or the ports may be spaced apart longitudinally. In still other embodiments, three, four, or more channels 210 may be created.

FIG. 5A is a cross-sectional side view of an example mandrel 500. In some embodiments, the mandrel 500 may have at least one depression 510 configured to receive the distal end of the crescent shaped mandrel 200. The at least one port 112 in the inner liner 110 may be created over the depression 510. As shown, the mandrel 500 includes two depression 510 spaced apart longitudinally and offset radially. The depression 510 may serve to lock the crescent shaped mandrel 200 in place during manufacture. The at least one depression 510 may be used to create one or more ports 112 in the inner liner 110 of the guide catheter 100, as discussed above with reference to FIGS. 3A-3G. The ports 112 may be created along the length of the inner liner 110 or over only a distal portion of the inner liner 110. The inner liner 110 may be formed using suitable biocompatible material including, but not limited to, TFE, or the like. The depression 510 may have any suitable shape or size including: crescent, circular, rectangular, and the like. In some embodiments, the depression 510 is shaped to complement the distal end of the crescent shaped mandrel 200. Similarly, the ports 112 may have a suitable shape or size including but not limited to, crescent, circular, rectangular, polygonal, "S" shaped, and the like. In one embodiment, differently shaped ports may be present along the length of the catheter or over a portion of the inner liner 110. The ports 112 may be laser cut into the inner liner 110, as discussed herein.

Figure 5B:
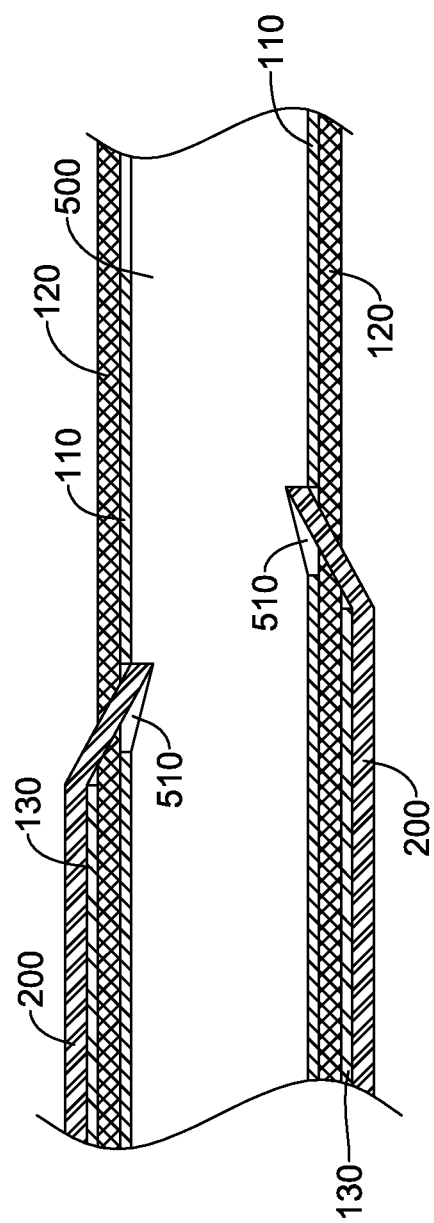
FIG. 5B is a longitudinal cross-sectional side view showing a manufacturing step of an example guide catheter using the mandrel of FIG. 5A.

FIG. 5B is a cross-sectional side view showing a manufacturing step, similar to that discussed herein with reference to FIGS. 3C-3D. As discussed above, the braid 120 may be disposed over the inner liner 110 after ports 112 are cut. The first polymer layer 130 may be placed over the braid 120, and then the distal ends of crescent shaped mandrels 200 may be inserted through the interstices of the braid 120, through ports 112 in the inner liner 110, and into the depressions 510. Thereafter, the second polymer layer 140 is placed over the crescent shaped mandrel 200, and the first polymer layer 130 and second polymer layer 140 are reflowed over the catheter shaft. The crescent shaped mandrels 200 and the mandrel 500 are removed, leaving a catheter with an inner lumen and channels 210 in fluid communication with the inner lumen. The density of the first polymer layer 130 and the second polymer layer 140 may differ.

FIG. 6A is a cross-sectional side view of another exemplary guide catheter 600. In another embodiment, a channel 620 is formed in a guide catheter 600 using a component that is left in place instead of using a crescent shaped mandrel that is removed after assembly. As shown, the guide catheter 600 may include shaft 610 including one or more microtube channels 620. In this embodiment, the crescent shaped channel 210 (e.g., as discussed with respect to FIG. 1) is replaced by the microtube channel 620. Each of the microtube channels 620 may be defined by a very small diameter tube that may have a very thin wall. The microtube channels 620 may be formed using a suitable material or polymer tube that is compatible with the bonding process, and may contribute to the strength of laminations of the catheter 600. One or more microtube channels 620 may be embedded within the guide catheter 600 during manufacture. The microtube channels 620 may extend to the distal end face 615 of the catheter, such that contrast media may be released from the distal end face 615 of the catheter. In other embodiments, the microtube channels 620 may extend to ports (not shown) in fluid communication with an inner lumen 605 of the catheter 600, such that contrast media may be released into the inner lumen 605 of the catheter 600.

Each of the microtube channels 620 may be filled with one or more spacers or beads 630. An interstitial space may be defined between the beads 630 to allow passage of fluid. The one or more beads 630 may prevent the channels 620 from being entirely closed off when compressed about a bend in the catheter 600. The beads 630 may have any suitable size or shape including, but not limited to, circular, rectangular, zigzag, polygonal, irregular, and the like. In some embodiments, the channel 620 may include beads 630 of the same size and/or shape. In alternate embodiments, the channel 620 may include beads 630 of varying size and/or shape. For example, 30 percent of the beads 630 may be more than half of the size of the channel 620 and 30 percent of the beads 630 may be less than one fourth of the size of the channel 620, and 40 percent of the beads 630 may be flat with length, width and thickness greater than half of that of the channel 620. The beads 630 may be composed of a suitable polymer that will not melt or flow during bonding so that the shape and size of the beads 630 remains unchanged. The beads 630 may have irregular shapes to create more interstitial space between them. The one or more beads 630 may each be hollow. In an alternate embodiment, the beads 630 may be solid. In yet another embodiment, the beads 630 may be porous to allow the fluid to pass through them. The beads 630 may be made up of suitable biocompatible metal or alloys. The beads 630 may remain fixed within the microtube channels 620 so that they do not move when fluid passes through the microtube channels 620. In other embodiments, the beads 630 may float freely within the microtube channels 620, with a screen 650 or porous plug 660 disposed within the channel 620 at the distal end face 615. The screen 650 or plug 660 may aid in retaining the beads 630 within the channel 620 when the channel 620 is flushed or when contrast media is passed through the channel 620. The screen 650 or plug 660 may include a foam with an open cell size less than or equal to one-half the smallest dimension of the beads 630. FIGS. 6B and 6C are partial views of alternative embodiments, showing only portion 640 from FIG. 6A.

A method of filling the channels 620 with beads 630 may involve suspending the beads in a slurry. The slurry may be composed of a mixture of a viscous liquid and the beads 630. For example, the beads could be within a slurry of liquid soap such as dishwashing soap. The slurry may then be injected into the channel 620. The distal end of the channel may be temporarily blocked off, so that the slurry is contained within and fills the channel 620. Once the channel is filled, the temporary distal closure may be removed. The permanent distal port screen 650 or porous plug 660 may prevent the beads 630 from passing, but allows the slurry liquid to be flushed out of the channel with a liquid such as water or a solvent. This process may be repeated multiple times until the channel 620 is sufficiently filled with beads 630. The channel containing beads may then be allowed to dry.

Alternatively, a solgel may be introduced into the channel 620 and the solids may be allowed to settle out of the gel via sedimentation while the catheter is lying horizontally. After sedimentation has occurred, the catheter may be raised to a vertical orientation to allow the liquid portion of the solgel to drain and dry out. This process may be repeated until the channel is sufficiently filled with beads. Examples of particles or beads deposited from solgels may include silicon oxides and titanium oxides.

Another method of filling the channel 620 with beads 630 may be to utilize a heated supersaturated solution of solvent and solute. The channel may be filled with the heated supersaturated solution. The contents may be allowed to cool, and solute may then precipitate to form the particles or beads 630. The precipitates may be selected so as to not be readily soluble in solutions that would be passed through the channel during the use of the device in the medical procedure; e.g., saline solution and radiographic contrast solution at ambient temperature. An example of a supersaturated solution and precipitate may include sodium orthophosphate in water. For example, 1.5 grams (0.05291 ounce) of the solute is soluble in 100 cc of cold water, while 157 grams (5.538 ounces) of solute is soluble in 100 cc of hot water. Another example is sodium pyrophosphate in water. 5.41 grams (0.1908 ounce) of solute is soluble in 100 cc of cold water, while 93.11 grams (3.284 ounces) is soluble in 100 cc of hot water. (CRC Handbook of Chemistry and Physics, 62nd edition, 1981-1982, CRC Press, pages B148-B150.)

Figure 7:
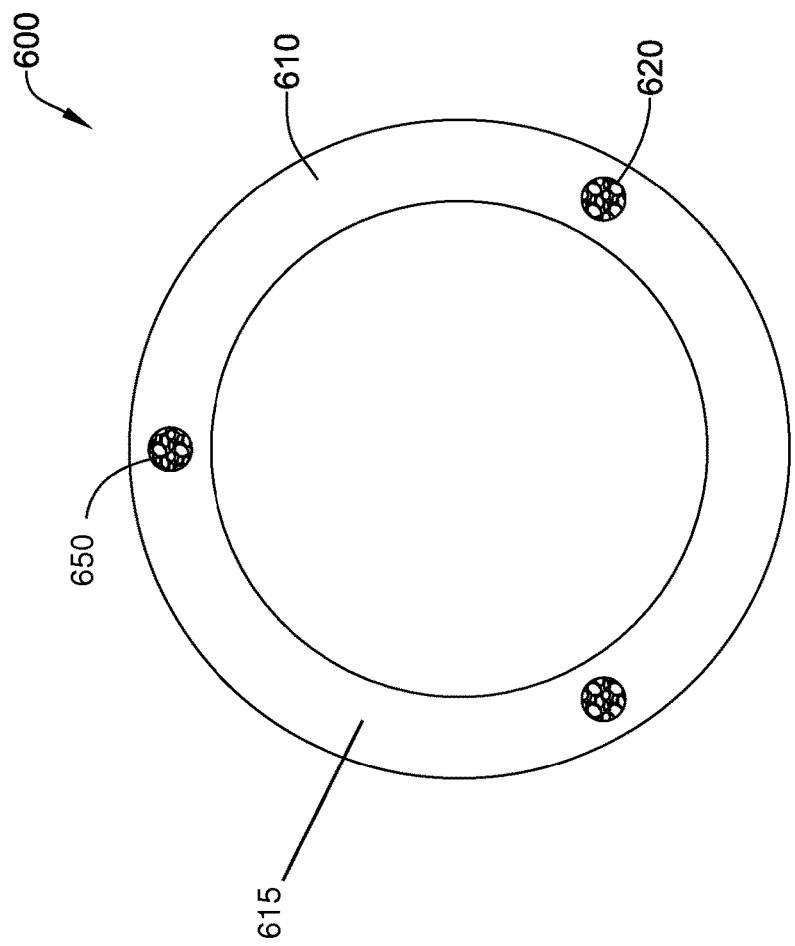
FIG. 7 is an end view of the distal end of the guide catheter of FIG. 6A.

FIG. 7 is an end view of the guide catheter of FIG. 6 showing the distal end face 615. As shown, the shaft 610 may include one or more microtube channels 620 spaced apart around the circumference of the catheter 600. The channels 620 may have a screen 650 or plug 660 disposed in the distal end.

Figure 8:
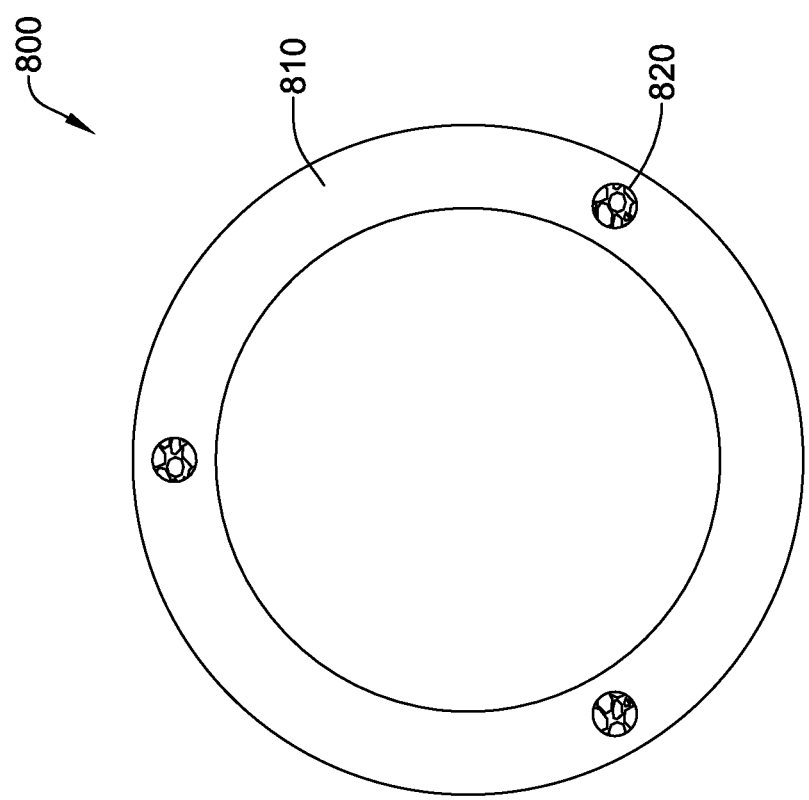
FIG. 8 is a transverse cross-sectional view of another example guide catheter.

FIG. 8 is a transverse cross-sectional view of another exemplary guide catheter 800. As shown, the guide catheter 800 may include a shaft 810. The guide catheter 800 is similar in structure and/or functionality to the guide catheter 100 except that the shaft 810 or a channel within the shaft 810 may include one or more elongate elements or filaments 820. Each of the filaments 820 may be a porous member. The filaments 820 may be made by a method or process that produces interconnected porosity within the filament 820. In one embodiment, the one or more filaments 820 may be formed using suitable porous plastic components, such as, plastic components manufactured by the Permaplas Corporation (Fayetteville, Ga.). The filaments 820 may extend to ports (not shown) in fluid communication with an inner lumen of the catheter 800 near the distal end of the catheter. In some embodiments, the filaments 820 may extend near the distal end face 615, and a screen 650 or porous foam plug 660 may be disposed between a distal end of the filaments 820 and the distal end face 615 of the catheter 800. The screen 650 or plug 660 may aid in retaining the filaments 820 within a channel or within the wall of the catheter 800. In some embodiments, the distal end of the filament 820 may be attached to an inner surface of a channel at the distal end face 615. Such an attachment may secure the filament 820 and prevent the filament 820 from being dislodged when contrast media is passed through the filament. The filament 820 may be attached to the catheter shaft 810 with medical adhesive.

Figure 9:
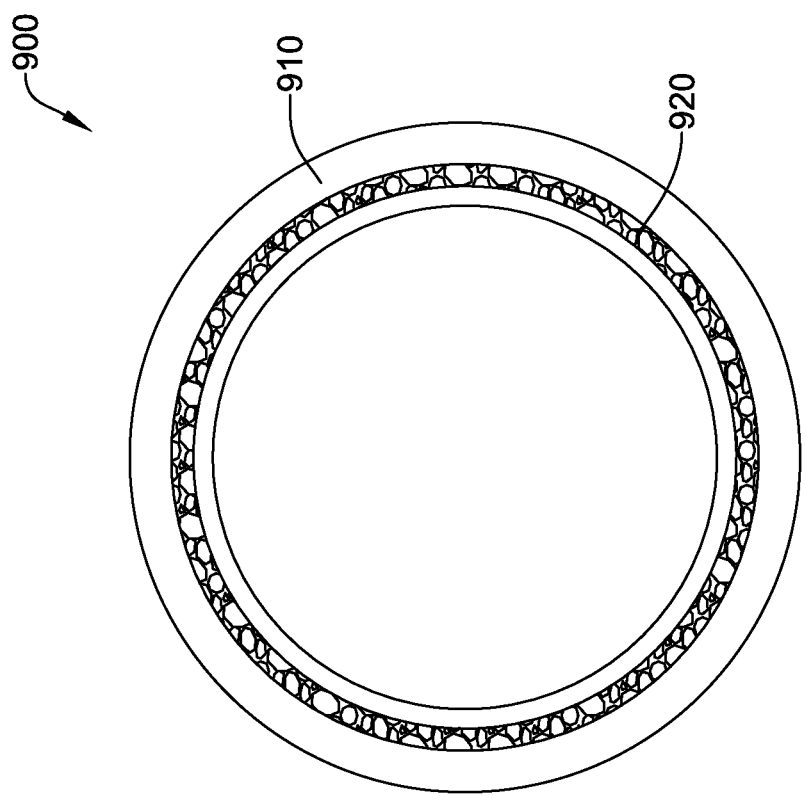
FIG. 9 is a transverse cross-sectional view of another example guide catheter.

FIG. 9 is a transverse cross-sectional view of another example guide catheter 900. As shown, the guide catheter 900 may include a shaft 910 including a porous layer or tube 920 embedded within the catheter wall. The porous tube 920 may be a porous polymer sleeve in communication with ports (not shown) in fluid communication with an inner lumen of the guide catheter 900 near the distal end of the catheter. The porous tube 920 may be made by a method or process that produces interconnected porosity within the porous tube 920. In one embodiment, the porous tube 920 may be formed using porous plastic components of Permaplas Corporation (Fayetteville, Ga.).

Figure 10:
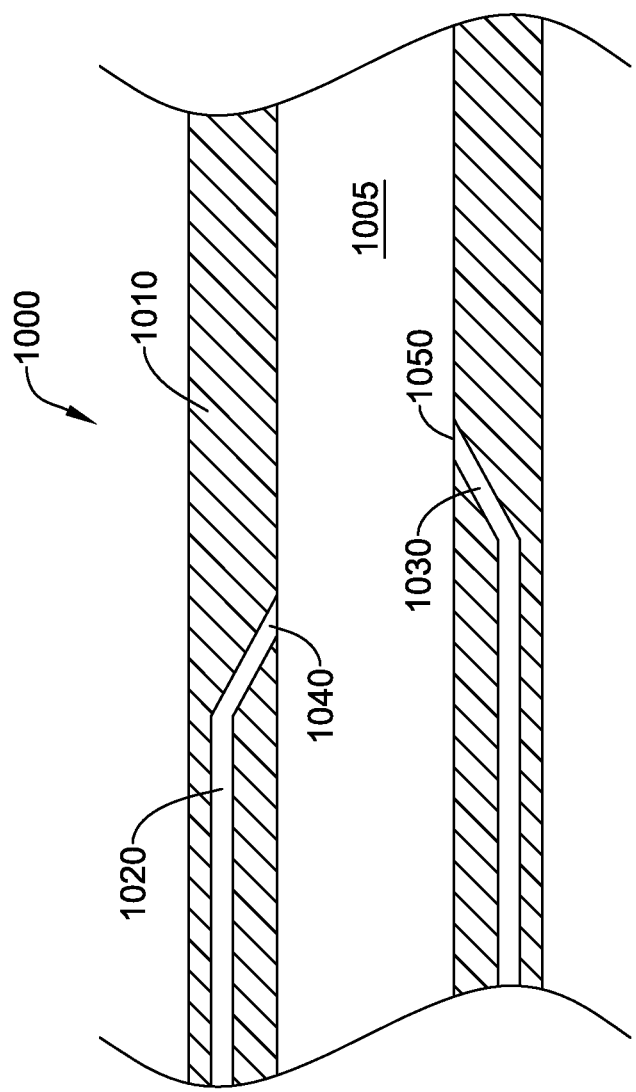
FIG. 10 is a longitudinal cross-sectional side view of another example guide catheter.

FIG. 10 is a cross-sectional side view of another exemplary guide catheter 1000. The guide catheter 1000 may include a shaft 1010. The shaft 1010 may include at least one channel 1020 pre-filled with contrast medium 1030. Further, each channel 1020 may include a port 1040 in fluid communication with a lumen 1005 of the shaft 1010. The guide catheter 1000 is similar in structure to the guide catheter 100 of FIG. 1, except that the port 1040 may include a film or frangible member 1050 disposed over the port 1040 to control the movement of the contrast medium 1030 into the catheter 1000. The inner liner, braid and polymer layers are not shown for simplicity. The film or frangible member 1050 disposed over the port 1040 may be configured to transition from a first configuration to a second configuration upon application of a predetermined fluid pressure through the channel 1020. In the first configuration, the port 1040 may remain closed, and in the second configuration the ports 1040 may open. The film may transition from the first configuration to the second configuration when enough hydraulic pressure is exerted upon the film. The film 1050 may be configured to rupture upon application of a predetermined amount of pressure. In other embodiments, the film 1050 may have a slit which remains closed when no pressure is applied but opens upon application of a predetermined amount of pressure. This embodiment allows for opening and closing the film 1050 to provide periodic injection of contrast medium during a procedure. In one embodiment, the hydraulic pressure may be exerted upon the film with an injection system. In an exemplary scenario, when the contrast medium 1030 is to be delivered into a vessel of the patient, an injection system may only have to push the pre-filled contrast medium 1030 out of the catheter 1000.

A guide catheter 1000 with channels 1020 pre-filled with contrast medium 1030 may allow for faster application of contrast medium to a target site adjacent the distal end of the catheter and may require less pressure to deliver the contrast medium. This is because the contrast medium is already located at the port and once the required pressure to rupture or open the film or frangible member 1050, the contrast medium is delivered. This structure may be particularly advantageous with thicker or more viscous contrast medium or in situations where a larger volume of contrast medium is desired. As with the embodiments discussed above, the ports 1040 may be spaced apart longitudinally and offset radially, and may be disposed adjacent the distal end of the guide catheter 1000.

Pre-filled catheter 1000 may be made as discussed with reference to FIGS. 3A-3G. After the crescent shaped mandrels 200 are removed during manufacturing, the channels 1020 of the catheter 1000 may be filled with the contrast medium 1030. Alternatively, the channels 1020 may be filled with the contrast medium just prior to passing the catheter 1000 through the vasculature within the patient's body.

Figure 11:
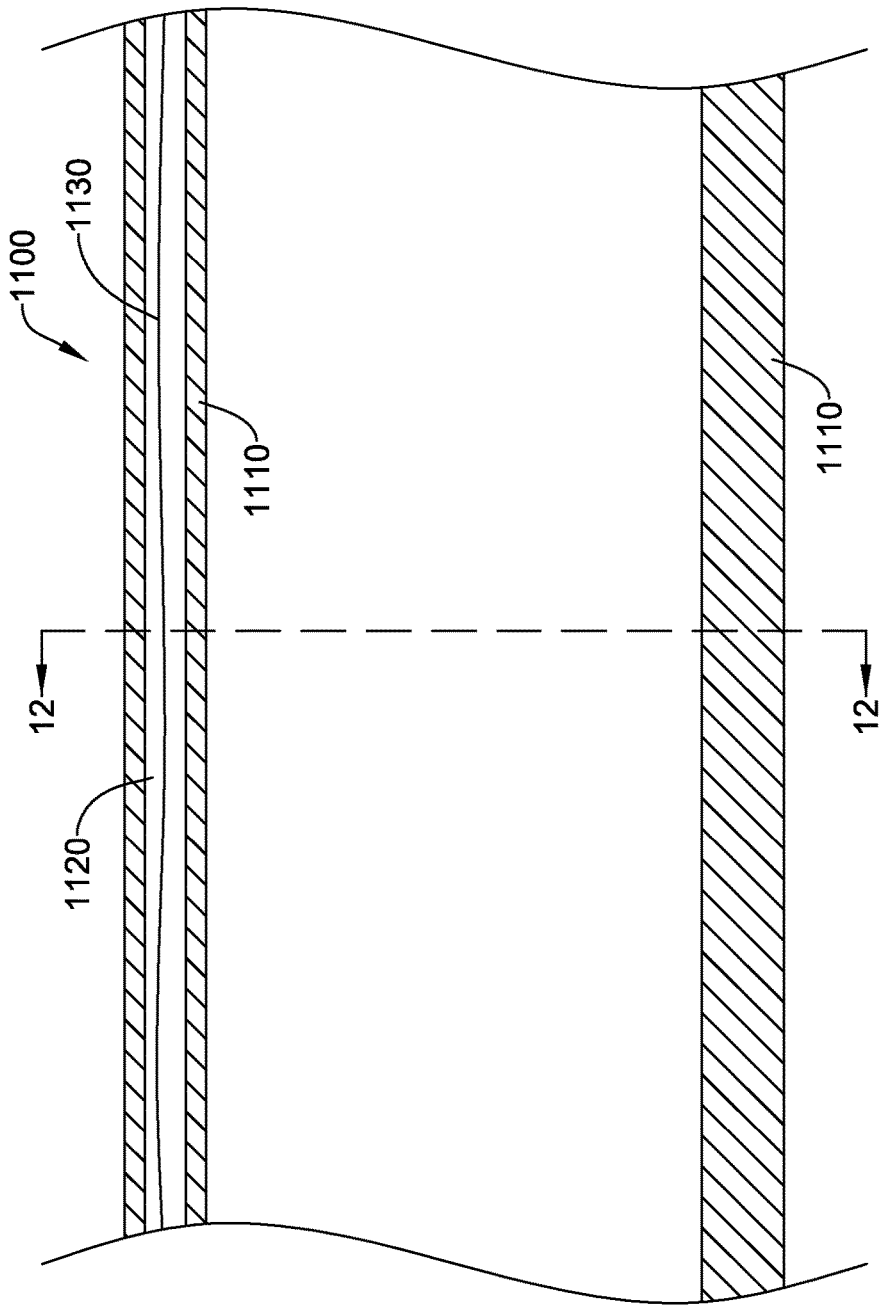
FIG. 11 is a longitudinal cross-sectional side view of another example guide catheter.

FIG. 11 is a cross-sectional side view of another exemplary guide catheter 1100. As shown, the guide catheter 1100 may include a shaft 1110, a channel 1120, and a spacer. The spacer may be an elongate element, such as a filament 1130. The filament 1130 may be formed using suitable biocompatible materials including, but not limiting to, stainless steel, aluminum, gold, platinum, titanium, PET, PVC, Polycarbonate, nylon, silk, PEEK, or the like. The guide catheter 1100 is similar in functionality and/or structure to the guide catheter 100 as described in FIG. 1, except that the channel 1120 may include a spacer or filament 1130 having a small diameter. The inner liner, braid, and polymer layers are not shown in FIG. 11 for simplicity. The spacer or filament 1130 may run axially through the entire length of the crescent shaped channel 1120. In an embodiment, the spacer or filament 1130 may run through only a portion within the catheter 1100. The spacer or filament 1130 may prevent complete collapse and closure of the crescent shaped channel 1120 when the guide catheter 1100 is severely bent. The filament 1130 may be of a size that may take up only a portion of open space of the channel 1120.

During the manufacturing process as described in FIGS. 3A-3G, the spacer or filament 1130 may be inserted within a bore hole in a crescent shaped mandrel (similar to crescent shaped mandrel 200 of FIG. 2) such that the crescent shaped mandrel may be removed after catheter 1100, but the filament 1130 may be left in place. Alternatively, the spacer or filament 1130 may be inserted into the channel 1120 after the mandrel is removed.

Figure 12:
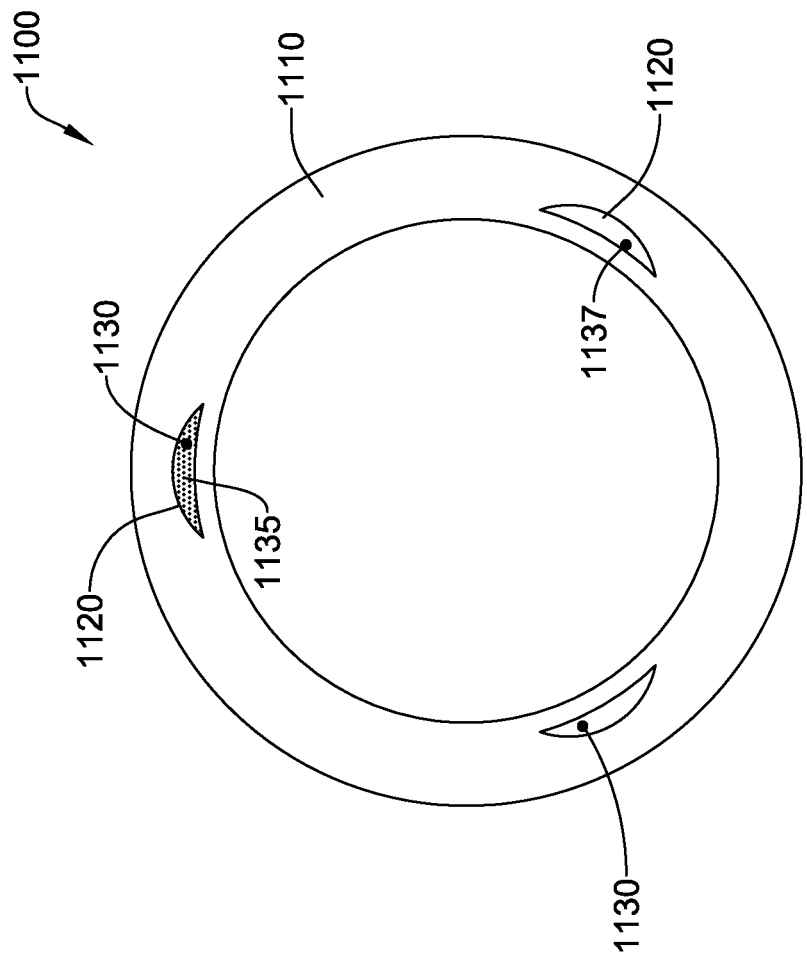
FIG. 12 is a transverse cross-sectional view taken through line 12-12 in FIG. 11.
Figure 13A:
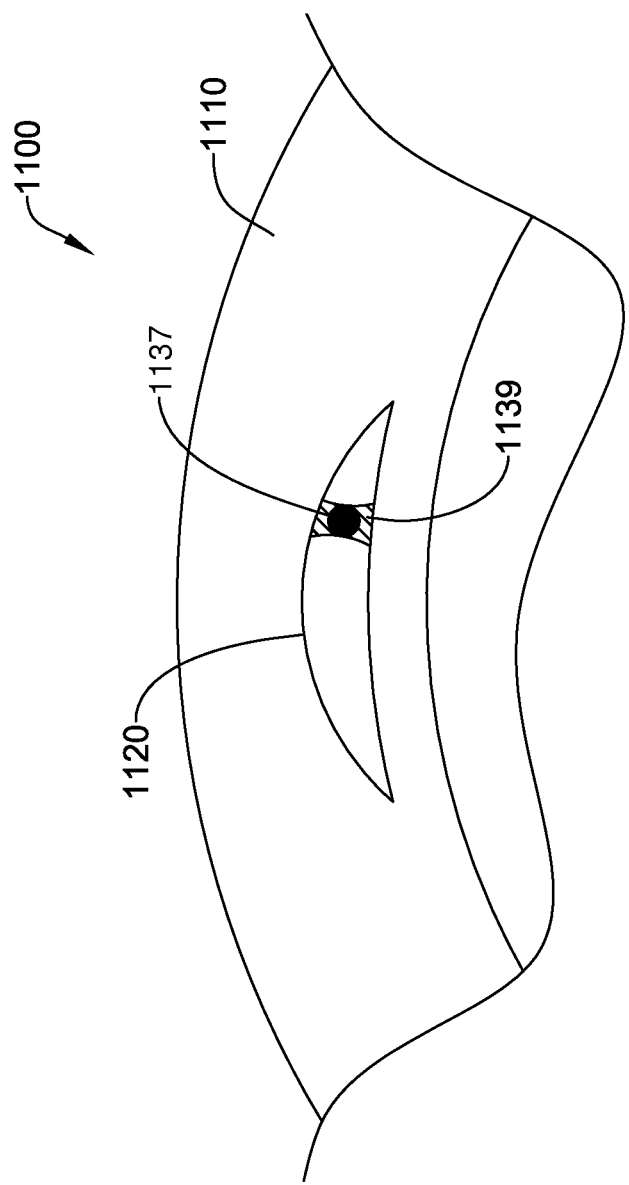
FIG. 13A is a partial transverse cross-sectional view of the guide catheter of FIG. 12.
Figure 13B:
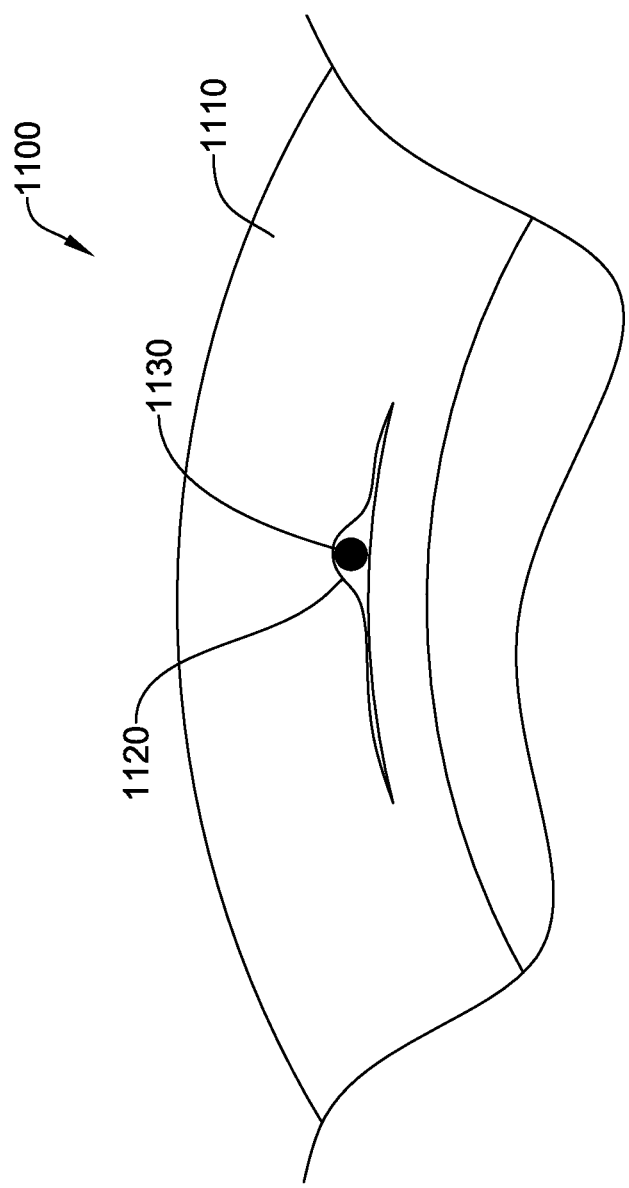
FIG. 13B is a partial cross-section view of the guide catheter of FIG. 13A in a bent configuration.

FIG. 12 is a cross-sectional view taken through line 12-12 of the guide catheter 1100 shown in FIG. 11. The filament 1130 may be disposed axially within the channel 1120 of the guide catheter 1100. The filament 1130 may prevent complete closure of the channel 1120 when the catheter 100 is bent. As with previous embodiments, a plurality of channels 1120 may be spaced apart around the circumference of the shaft 1110. The filament 1130 may extend all the way to the port near the distal end of the catheter 1100. Alternatively, the filament 1130 may be disposed proximal of the port. A screen or porous plug 1135 may be placed at the distal end of the channel 1120. The distal end 1137 of the filament may be attached to an inner surface of the channel 1120. In some examples, an adhesive 1139 may be used to attach the distal end 1137 to the inner surface of the channel 1120. FIG. 13A is a partial cross-sectional view of the guide catheter 1100 from FIG. 12, showing one of the channels 1120 in more detail. The channel 1120 is shown with the filament 1130 in the channel 1120 in an open configuration. In this example, the distal end 1137 of the filament 1130 is shown attached to the inner surface of the channel 1120 with adhesive 1139. FIG. 13B shows the guide catheter of FIG. 13A in a bent configuration with the channel 1120 partially collapsed. If the channel 1120 starts to collapse as the catheter bends, the internal filament 1130 may keep the channel partially open. Therefore, even if the channel 1120 collapses over a period of time or due to severe bending of the catheter 1100, the filament 1130 still keeps the channel 1120 partially open and allows fluid to flow through the channel 1120.

The materials that can be used for the various components of the guide catheter 100 (and/or other devices disclosed herein) may include those commonly associated with medical devices. For simplicity purposes, the following discussion makes reference to the guide catheter 100. However, this is not intended to limit the devices and methods described herein, as the discussion may be applied to other similar tubular members and/or components of tubular members disclosed herein.

In some embodiments, the beads 630, filaments 820, porous tube 920, or filament 1130 are made of a bioabsorbable material. In the event a portion of these materials is liberated from the catheter, the material would harmlessly decompose into chemicals and minerals already present in the body. Bioabsorbable materials may include polymers such as polyglycolic acid, polylactic acid (PLA), polyhydroxyalkanoates (PHAs) polycaprolactone, polylactic acid-polyethylene oxide copolymers, cellulose, collagens, chitins, and combinations thereof, and the like. Bioabsorbable metals such as magnesium and magnesium alloys may also be used.

The guide catheter 100 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the guide catheter 100 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guide catheter 100 in determining its location.

Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guide catheter 100 to achieve the same result. In some embodiments, a degree of Magnetic Resonance Imaging (MRI) compatibility may be imparted into the guide catheter 100. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the guide catheter 100 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one exemplary embodiment in other embodiments. The disclosure's scope is, of course, defined in the language in which the appended claims are expressed.

What is claimed is:

1. An intravascular catheter, comprising:
an elongate shaft defined by a wall and having a proximal end, a distal end, and a lumen extending therebetween, the shaft having a length extending between the proximal and distal ends, the shaft having at least one port extending through the wall into the lumen;
a first layer disposed over the shaft, the first layer extending from the proximal end of the shaft over the at least one port to a distal terminus;
a second layer disposed over the first layer;
a third layer disposed over the second layer; and
at least one channel defined between the second and third layers, the at least one channel extending along at least a portion of the shaft and into the at least one port, wherein the at least one channel extends around less than an entire circumference of the shaft; wherein a first cross-sectional thickness of the catheter measured from the lumen through the elongate shaft, first layer, second layer, at least one channel, and third layer is substantially the same as a second cross-sectional thickness in a region without a channel, measured from the lumen through the elongate shaft, first layer, second layer, and third layer, along the length of the shaft.

2. The catheter of claim 1, wherein the first layer includes a braid defining a plurality of interstices, wherein the at least one channel extends through an interstice of the braid.

3. The catheter of claim 1, wherein a cross section of the at least one channel taken perpendicular to a longitudinal axis of the shaft has a substantially crescent shaped cross section.

4. The catheter of claim 1, wherein the at least one port includes a plurality of ports offset longitudinally from one another.

5. The catheter of claim 1, further comprising a film disposed over each of the at least one port, wherein the film over each of the at least one port is configured to rupture upon application of a predetermined fluid pressure through the at least one channel.

6. The catheter of claim 1, further comprising an elongate element disposed longitudinally within the at least one channel.

7. The catheter of claim 1, further comprising a plurality of beads disposed within the at least one channel.

8. The catheter of claim 1, wherein the at least one port includes a plurality of ports, wherein the plurality of ports are spaced apart longitudinally along a region of the shaft.

9. An intravascular catheter, comprising:
an elongate shaft having a proximal end, a distal end and a lumen extending therebetween, the elongate shaft including:
an inner liner having a wall and defining the lumen, the inner liner having at least one port extending through the wall into the lumen;
a braid disposed over the inner liner, the braid extending over the at least one port;
a first polymer layer disposed over the braid;
a second polymer layer disposed over the first polymer layer; and
at least one channel defined between the first and second polymer layers and extending along the elongate shaft and into the at least one port;
wherein an inner diameter and an outer diameter of the elongate shaft are substantially constant along an entire length of the elongate shaft.

10. The catheter of claim 9, wherein the at least one channel includes a porous layer.

11. The catheter of claim 9, wherein the at least one port includes a plurality of ports, wherein the plurality of ports are spaced apart longitudinally along a region of the elongate shaft.

* * * * *